(12) United States Patent
Otera et al.

(10) Patent No.: US 7,115,736 B2
(45) Date of Patent: Oct. 3, 2006

(54) PROCESS FOR PREPARING IMIDAZOPYRAN DERIVATIVES

(75) Inventors: Junzo Otera, Okayama (JP); Akihiro Orita, Okayama (JP)

(73) Assignee: Daiso Co., Ltd., Osaka (JP)

( * ) Notice: Subject to any disclaimer, the term of this patent is extended or adjusted under 35 U.S.C. 154(b) by 0 days.

(21) Appl. No.: 11/227,097

(22) Filed: Sep. 16, 2005

(65) Prior Publication Data

US 2006/0063929 A1    Mar. 23, 2006

(30) Foreign Application Priority Data

Sep. 17, 2004   (JP)   ............... 2004-271015

(51) Int. Cl.
  *C07D 498/04*   (2006.01)
  *C07D 233/66*   (2006.01)
(52) U.S. Cl. ..................... 544/92; 548/327.5
(58) Field of Classification Search ............ 544/92; 548/327.5
See application file for complete search history.

(56) References Cited

U.S. PATENT DOCUMENTS 6,087,358 A   7/2000  Baker et al.

FOREIGN PATENT DOCUMENTS

WO    97/01562    1/1997

OTHER PUBLICATIONS

Krysztof Walczak et al., "Synthesis of Acyclic Nitroazole Nucleosides and Their Incorporation into Oligonucleotides, and Their Duplex and Triplex Formulation", Helvetica Chimica Acta, vol. 87, pp. 469-478, XP002354143, Feb. 2004.

Sanzhong Luo et al., "Ytterbium Triflate Catalyzed Reactions of Epoxide with Nitrogen Heterocycles Under Solvent-Free Condition", Synthetic Communications, vol. 33, No. 17, pp. 2989-2994, XP009057051, 2003.

Kelvin K. Ogilvie et al., "A general method for selective silylation of primary hydroxy groups in carbohydrates and related compounds", Carbohydrate Research, vol. 115, pp. 234-239, XP002354144, 1983.

Theodora W. Greene et al., "Protective Groups in Organic Synthesis", John Wiley & Sons, Inc., pp. 86-119, XP002354152, 1991.

*Primary Examiner*—Kahsay Habte
(74) *Attorney, Agent, or Firm*—Wenderoth, Lind & Ponack, L.L.P.

(57) ABSTRACT

A novel process for preparing imidazopyran derivatives of the formula:

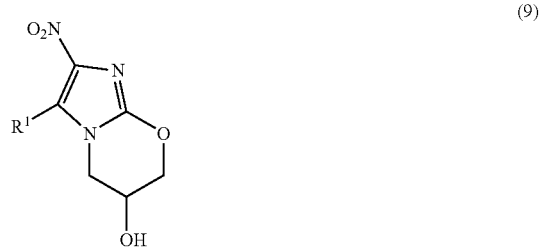

(9)

wherein $R^1$ is halogen atom, hydrogen atom, $C_1$ to $C_3$ alkyl group, aryl group, or aryl group substituted by $C_1$ to $C_3$ alkyl group, by using dinitroimidazole and 2,3-epoxy-1-propanol as starting materials and being followed by five steps.

18 Claims, No Drawings

PROCESS FOR PREPARING IMIDAZOPYRAN DERIVATIVES

TECHNICAL FIELD

The present invention relates to a process for preparing an imidazopyran derivative, its intermediate and a process for preparing thereof.

BACKGROUND OF THE INVENTION

An imidazopyran derivative of the following formula (9A) is useful as, for example, an intermediate of PA-824 having the following formula, which has antibacterial activity against Mycobacterium tuberculosis and so on.

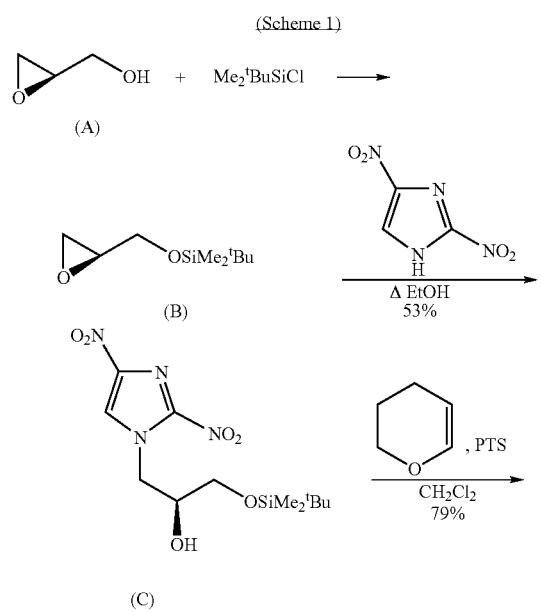

The process for preparing imidazopyran derivatives is known and shown by the following scheme 1 (see WO 97/01562).

According to this process, the compound (B) obtained starting from glycidol and t-butyldimethylsilyl ether is reacted with 2,4-dinitroimidazole, and after protecting the hydroxy group of the resulted siloxy alcohol (C) with dihydropyran, the tetrahydropyranyl (THP) ether compound (D) is subjected to desilylation and cyclization to form imidazopyran skeleton (E) and then, the imidazopyran derivative (F) is obtained by removal of THP group.

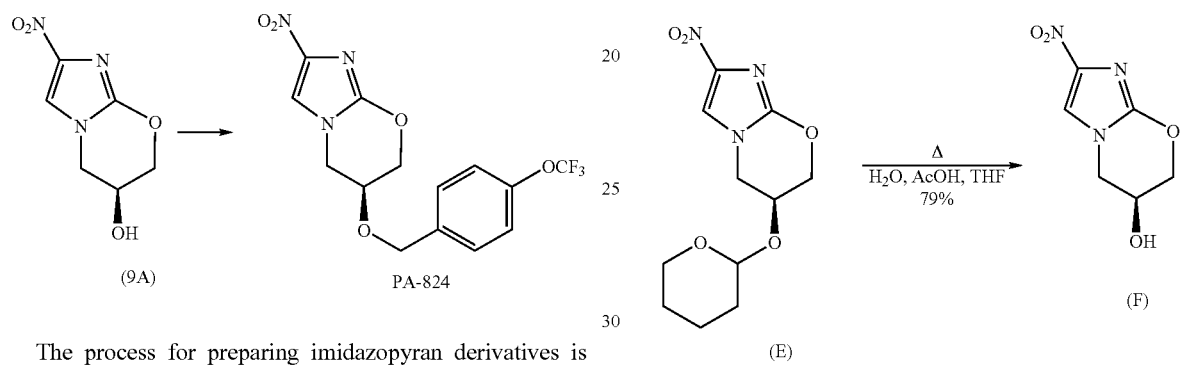

DETAILED DESCRIPTION OF THE PREFERRED EMBODIMENTS

However, according to this known method, after glycidol t-butyldimethylsilyl ether (B) is once prepared from glycidol (A) and is isolated, the compound have to be reacted with dinitroimidazole and the procedure is troublesome. The yield of compound (C) from compound (A) is less than 50%, and the yield of compound (F) from compound (C) is 46%.

The present inventors have extensively studied to dissolve the above problems, and found the effective process for preparing imidazopyran derivatives by using 2,3-epoxy-1-propanol and dinitroimidazole as starting materials. Thus the present invention was completed.

Namely, the present invention relates to a process for preparing an imidazopyran derivative shown below. The present invention relates to also its intermediate and a process for preparing the intermediate, as shown below.

The reaction process related to the present invention is shown as following reaction scheme 2.

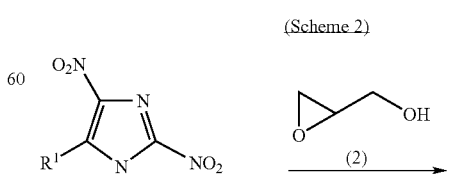

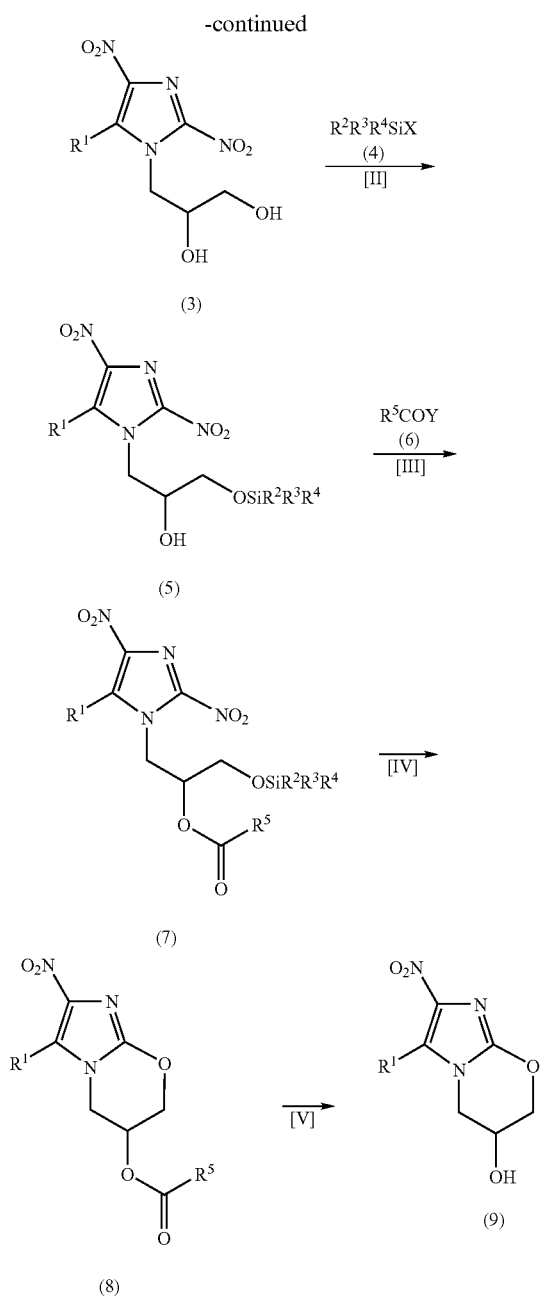

wherein, $R^1$ is halogen atom, hydrogen atom, $C_1$ to $C_3$ alkyl group, aryl group, or $C_1$ to $C_3$ alkyl group substituted by aryl group, $R^2$, $R^3$ and $R^4$ are independently $C_1$ to $C_6$ alkyl group, aryl group or $C_1$ to $C_3$ alkyl group substituted by aryl group, $R^5$ is aryl group or $C_2$ to $C_4$ alkenyl group substituted by aryl group, X is halogen atom, and Y is halogen atom, hydroxy group or an alkoxy group.

According to the present invention, an imidazopyran derivative is more effectively prepared comparing with the known method.

Furthermore, according to the present invention, the process from step I to step II, and the process from step III to step V are carried out in one pot method, respectively. Therefore, when the reaction is carried out as such, the procedure in the process is simple and the yield surprisingly increases comparing with carrying out each reaction step by step.

The above process related to the present invention is explained along the line of each step.

(Step I)

A diol compound of the formula (3) is prepared by reacting a dinitroimidazole of the formula (1) and 2,3-epoxy-1-propanol of the formula (2) in the presence of a fluoride salt.

$R^1$ of a compound of the formula (1) includes preferably methyl group, ethyl group, n-propyl group, isopropyl group, chlorine atom, bromine atom, hydrogen atom and benzyl group, and especially preferably hydrogen atom. For example, 2,4-dinitroimidazole is easily prepared by nitrating commercialized 4-nitroimidazole with a nitrating agent such as fuming nitrous acid.

On the other hand, a compound of the formula (2) is easily prepared by treating 3-chloro-1,2-propanediol with a base.

The fluoride salt includes an alkali metal fluoride and an alkaline earth metal fluoride, especially preferably cesium fluoride. When cesium fluoride is used, its amount is 0.01 to 0.5 molar equivalents, especially preferably 0.05 to 0.3 molar equivalents.

The solvent is, if necessary, used, but the reaction is preferably carried out in the absence of solvents.

The reaction temperature is preferably −10 to 50° C., especially preferably 10 to 35° C. The reaction is carried out at a range of ordinary pressure to 1 MPa. The reaction is continued until the starting material(s) are disappeared, usually for 3 hours to 24 hours.

Resulted compound (3) can be used in next step without purification, but may be purified and isolated with conventional purification methods such as column chromatography.

(Step II)

Then the siloxy alcohol derivative of the formula (5) is prepared by reacting a diol compound of the formula (3) with a silyl halide in the presence of a base.

The examples of the compound of the formula (4) are ones wherein $R^2$, $R^3$ and $R^4$ are independently methyl group, ethyl group, n-propyl group, isopropyl group, n-butyl group, t-butyl group, phenyl group, benzyl group, phenethyl group, and so on, and especially preferably methyl group, ethyl group, isopropyl group and phenyl group. The amount of silyl halide (4), especially silyl chloride is more than 1 molar equivalent, preferably 1.1 to 1.8 molar equivalents from the view point of reactivity and after-treatment.

The base used herein includes an amine such as triethylamine, diisopropylethylamine, pyridine, imidazole, 1,8-diazabicyclo[5,4,0]undec-7-ene (DBU), etc., an alkali metal carbonate such as potassium carbonate, sodium carbonate, sodium hydrogencarbonate, cesium carbonate, etc., and a hydroxide such as sodium hydroxide, potassium hydroxide, calcium hydroxide, etc. Among them, imidazole is preferable. The amount of the base is more than 1 molar equivalent, especially preferably 2 to 5 molar equivalents.

Furthermore, co-catalyst such as 4-N,N-dimethylaminopyridine may be co-existed, and the amount is 1 mole % to 20 moles %.

The reaction is preferably conducted in the state of compound (3) diluted by a solvent. The solvent is not limited as far as it can dissolve compounds (3) and (4), and does not react with said materials. The solvent includes preferably a hydrocarbon-solvent such as hexane, benzene, toluene, etc., a chlorinated solvent such as chloroform, 1,2-dichloroethane, dichloromethane, etc., a nitrile-solvent such as acetonitrile, etc., and an ether-solvent such as diethyl ether, diisopropyl ether, t-butyl methyl ether, cyclopentyl methyl ether, tetrahydrofuran, etc., an aprotic polar solvent such as N,N-dimethylformamide, dimethyl sulfoxide, etc. and especially preferably acetonitrile or N,N-dimethylformamide.

The reaction temperature is preferably more than 0° C., more preferably 20 to 40° C.

Thus obtained compound (5) can be purified and isolated with conventional purification methods such as column chromatography.

(Step III)

A dinitroimidazole derivative of the formula (7) is prepared by reacting a compound of the formula (5) with a compound of the formula (6).

As a compound of the formula (6) are illustrated a carboxylic acid, a carboxylic acid halide and a carboxylic acid alkyl ester. $R^5$ in the formula (6) means $C_6$–$C_{10}$ aryl group such as phenyl group and $C_2$–$C_4$ alkenyl group substituted by $C_6$–$C_{10}$ aryl group such as 2-phenylethenyl group. The amount of the compound (6) is 1 molar equivalent, preferably 1.1 to 1.8 molar equivalents.

In this reaction may be used a solvent preferably such as a hydrocarbon-solvent such as hexane, benzene, toluene, etc., chlorinated solvent such as chloroform, 1,2-dichloroethane, dichloromethane, etc., a nitrile-solvent such as acetonitrile, etc., an ether-solvent such as diethyl ether, diisopropyl ether, t-butyl methyl ether, cyclopentyl methyl ether, tetrahydrofuran, etc., or an aprotic polar solvent such as N,N-dimethylformamide, dimethyl sulfoxide, etc.

In addition, when the compound (6) is a carboxylic acid halide, especially a carboxylic acid chloride, a solvent such as an amine such as triethylamine, diisopropylethylamine, pyridine, 4-N,N-dimethylaminopyridine, etc., preferably pyridine may be used. When the compound (6) is a carboxylic acid, dichloromethane and tetrahydrofuran are especially preferable as a solvent.

When the compound (6) is a carboxylic acid, a condensing agent is preferably used. The condensing agent is preferably a carbodimide derivative, especially preferably dicyclocarbodiimide. In this reaction, a base may be co-used. The base includes an amine such as triethylamine, diisopropylethylamine, pyridine,4-N,N-dimethylaminopyridine, imidazole, DBU, etc., an alkali metal carbonate such as potassium carbonate, sodium carbonate, sodium hydrogencarbonate, cesium carbonate, etc., and a hydroxide such as sodium hydroxide, potassium hydroxide, calcium hydroxide, etc. Among them, 4-N,N-dimethyaminopyridine is preferable.

When the compound (6) is a carboxylic acid halide, especially carboxylic acid chloride, a base is preferably used. The base includes an amine such as triethylamine, diisopropylethylamine, pyridine,4-N,N-dimethylaminopyridine, imidazole, DBU, etc., an alkali metal carbonate such as potassium carbonate, sodium carbonate, sodium hydrogencarbonate, cesium carbonate, etc. and a hydroxide such as sodium hydroxide, potassium hydroxide, calcium hydroxide, etc. Among them, pyridine is preferable. An amine such as triethylamine, diisopropylethylamine, pyridine, 4-N,N-dimethyaminopyridine, etc. may be served as a solvent.

The reaction temperature, when the compound (6) is a carboxylic acid, is preferably more than 0° C., especially preferably 20 to 40° C. When the compound (6) is a carboxylic acid halide, especially a carboxylic acid chloride, the reaction temperature is preferably −20 to 20° C., especially preferably −5 to 10° C.

Thus obtained compound (7) can be used in next step without purification, but may be purified and isolated with conventional purification methods such as column chromatography.

The dinitroimidazole derivative (7) is not described in any literature. The dinitroimidazole derivative (7) wherein $R^1$ is hydrogen atom, $R^2$, $R^3$ and $R^4$ are methyl group, or $R^2$ and $R^3$ are methyl group, $R^4$ is t-butyl group, and $R^5$ is phenyl group or 2-phenylethenyl group is preferable.

(Step IV)

Then, an imidazopyran ester derivative of the formula (8) is prepared by reacting compound (7) with a desilylation agent. By reacting the desilylation agent, the silyl group of the compound (7) is removed to give hydroxy group and then the hydroxy group attacks the carbon atom directly bound to nitro group, followed by cyclization to give the compound (8).

The desilylation agent is not limited as far as it can remove the silyl group, and includes a fluoride compound such as tetrabutylammonium fluoride, hydrogen fluoride.pyridine complex, cesium fluoride, etc., preferably tetrabutylammonium fluoride. The amount thereof to a substrate, compound (7) is more than 1 molar equivalent, preferably 1.1 to 2 molar equivalents.

A solvent used in this reaction includes preferably a hydrocarbon-solvent such as hexane, benzene, toluene, etc., a chlorinated solvent such as chloroform, 1,2-dichloroethane, dichloromethane, etc., a nitrile-solvent such as acetonitrile, etc., an ether-solvent such as diethyl ether, diisopropyl ether, t-butyl methyl ether, cyclopentyl methyl ether, tetrahydrofuran, etc., and an aprotic polar solvent such as N,N-dimethylformamide, dimethyl sulfoxide, etc., especially preferably tetrahydrofuran.

The reaction temperature is preferably more than 0° C., more preferably 20 to 100° C.

Thus obtained compound (8) can be used in next step without purification, but may be purified and isolated with conventional purification methods such as column chromatography.

An imidazopyran ester derivative (8) is not described in any literature. The imidazopyran ester derivative (8) wherein $R^1$ is hydrogen atom, $R^5$ is phenyl group or 2-phenylethenyl group is preferable.

(Step V)

Finally an imidazopyran derivative of the formula (9) is prepared by deprotecting the compound (8) in the presence of metallic catalyst.

The metallic catalyst used herein is preferably organic metallic catalyst having Lewis acidity. Titanium compound and stannous compound are preferable, and titanium tetraisopropoxide and bis(dibutylchlorotin)oxide belonged to titanium alkoxide are especially preferable. The amount of the metallic catalyst is 0.005 to 1.0 molar equivalent, preferably 0.01 to 0.7 molar equivalents.

The solvent used in this reaction includes an alcohol solvent such as methanol, ethanol, isopropanol, etc., a nitrile-solvent such as acetonitrile, etc., an ether-solvent such as diethyl ether, diisopropyl ether, t-butyl methyl ether, cyclopentyl methyl ether, tetrahydrofuran, etc., and an aprotic polar solvent such as N,N-dimethylformamide, dimethyl sulfoxide, etc. Among them the alcohol solvent is preferable, especially methanol.

The reaction is carried out at preferably more than 0° C., more preferably 40 to 100° C. and most preferably refluxing point of methanol.

Thus obtained compound (9) can be purified and isolated with conventional purification methods such as column chromatography.

(One Pot Method)

In the process for preparing an imidazopyran derivative (9) or its intermediate starting from 2,3-epoxy-1-propanol and dinitroimidazole of the present invention, it is not always necessary to isolate and purify the product in each step.

Namely the process from step I to Step II can be carried out in one pot and therefore, the product by step I can be successively subjected to the reaction of step II without isolation and purification.

Furthermore, the process from step III to Step V can be carried out in one pot and therefore, the product prepared by step III can be successively subjected to the reaction of step IV and Step V without isolation and purification of each product.

The present invention also relates to compounds (7) and (8). The present invention also relate to the process for preparing compound (5) starting from compounds (1) and (2), the process for preparing compound (7), (8) or (9) starting from compound (5), the process for preparing compound (8) starting from compound (7) and the process for preparing for compound (9) staring from compound (8).

(Optically Active Compound)

The intermediate compounds (3) to (8), and the final product (9) related to the present invention have an asymmetric carbon, and the optically active isomers exist respectively. The optically active isomers of dinitroimidazole derivatives (7), imidazopyran ester derivatives (8) and imidazopyran derivatives (9) can be prepared without racemization by using optically active 2,3-epoxy-1-propanol as a starting material.

EXAMPLE

The present invention is explained by following examples, but the present invention should not be limited to these examples.

Example 1

Synthesis of Compound (5a)

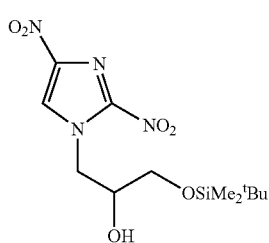

(5a)

Cesium fluoride (15 mg, 0.1 mmol) was put in a reaction vessel and the vessel was flame dried under an atmosphere of argon. 2,4-Dinitroimidazole (158 mg, 1 mmol) was added and glycidol (0.066 ml, 1 mmol) was dropped thereto. The mixture was stirred at room temperature for 12 hours.

After confirming the completion of the reaction with thin layer chromatography (TLC), the resulting diol compound was completely dissolved in N,N-dimethylformamide. Thereto were added imidazole (204 mg, 3 mmol) and N,N-dimethyl-4-aminopyridine (6 mg, 0.05 mmol) and the mixture was stirred for 30 minutes. Thereto was added t-butyldimethylsilyl chloride (301 mg, 2 mmol) and the mixture was stirred for 12 hours.

After confirming the completion of the reaction with TLC, the reaction was quenched with an aqueous saturated sodium hydrogencarbonate solution (5 ml). After removal of salts with Celite the filtrate was extracted with ethyl acetate (10 ml×3). The organic layer was washed with water (10 ml) and saturated brine (10 ml), successively, dried over anhydrous magnesium sulfate, concentrated with an evaporator in vacuo, and purified with silica gel column chromatography (ethyl acetate/hexane=3/7) to give compound (5a) in a 58% yield.

1H-NMR (500 MHz, DMSO-d6): δ 0.03 (s, 6H), 0.83 (s, 9H), 3.48 (dd, J=10.6 Hz, 6.7 Hz, 1H), 3.60 (dd, J=10.5 Hz, 4.9 Hz, 1H), 3.91 (m, 1H), 4.33 (dd, J=13.7 Hz, 8.85 Hz, 1H), 4.72 (dd, J=13.6 Hz, 3.05 Hz, 1H).

Example 2

Synthesis-1 of Compound (7a)

(7a)

A reaction vessel was flame dried under an atmosphere of argon. Thereto were added compound (5a) (346 mg, 1 mmol), benzoic acid (147 mg, 1.2 mmol), and N,N-dimethyl-4-aminopyridine (DMAP) (24.4 mg, 0.2 mmol), followed by addition of dichloromethane (5 ml) and the mixture was made completely homogeneous. Thereto dicyclohexylcarbodiimide (DCC) (0.84 ml, 1 mmol) was dropped and the mixture was stirred for 20 hours at room temperature.

After confirming the completion of the reaction with TLC, the reaction was quenched with an aqueous saturated sodium hydrogencarbonate solution (10 ml). The reaction mixture was extracted with ethyl acetate (10 ml×3). The organic layer was washed with water (10 ml) and saturated brine (10 ml), successively, dried over anhydrous magnesium sulfate, concentrated with an evaporator in vacuo, and purified with silica gel column chromatography (ethyl acetate/hexane=3/7) to give compound (7a) in a 86% yield.

1H-NMR (300 MHz, DMSO-d6): δ 0.06 (s, 6H), 0.82 (s, 9H), 3.95 (s, 2H), 4.79–4.97 (m, 2H), 5.45 (m, 1H), 7.48–7.67 (m, 3H), 8.87 (s, 1H).

Example 3

Synthesis-2 of Compound (7a)

A reaction vessel was flame dried under an atmosphere of argon. Thereto were added compound (5a) (346 mg, 1 mmol), and benzoyl chloride (0.174 ml, 1.5 mmol) and to the mixture was dropped at 0° C. pyridine (5 ml), followed by stirring for 15 hours.

After confirming the completion of the reaction with TLC, the reaction was quenched with an aqueous saturated sodium hydrogencarbonate solution (10 ml). The reaction mixture was extracted with ethyl acetate (10 ml×3). The organic layer was washed with water (10 ml) and saturated brine (10 ml), successively, dried over anhydrous magnesium sulfate, concentrated with an evaporator in vacuo, and purified with silica gel column chromatography (ethyl acetate/hexane=3/7) to give compound (7a) in a 77% yield.

Example 4

Synthesis-1 of Compound (7b)

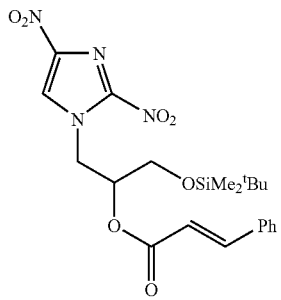

(7b)

Using cinnamic acid instead of benzoic acid, the reaction was conducted in the same manner as in Example 2 to give compound (7b) in an 86% yield.
1H-NMR (300 MHz, DMSO-d6): δ 0.05 (s, 6H), 0.79 (s, 9H), 3.85 (d, J=4.38 Hz, 1H), 4.85 (d, J=14.5 Hz, 1H), 5.30 (m, 1H), 6.47 (d, J=16.1 Hz, 1H), 7.39 (t, J=3.11 Hz, 3H), 7.54–7.63 (m, 3H), 8.79 (s, 1H).

Example 5

Synthesis-2 of Compound (7b)

Using cinnamoyl chloride instead of benzoyl chloride, the reaction was conducted in the same manner as in Example 3 to give compound (7b) in a 73% yield.

Example 6

Synthesis-1 of Compound (8a)

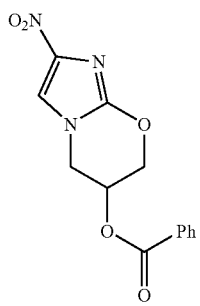

(8a)

A reaction vessel was flame dried under an atmosphere of argon. Thereto were added compound (7a) (450 mg, 1 mmol), followed by addition of tetrahydrofuran (5 ml) and the mixture was made completely homogeneous. Thereto tetrabutylammonium fluoride (TBAF) in 1M tetrahydrofuran solution (1.5 ml, 1.5 mmol) was dropped at 0° C. and the mixture was stirred for 3 hours at room temperature.

After confirming the completion of the reaction with TLC, the reaction was quenched with an aqueous saturated sodium hydrogencarbonate solution (10 ml). The reaction mixture was extracted with ethyl acetate (10 ml×3). The organic layer was washed with water (10 ml) and saturated brine (10 ml), successively, dried over anhydrous magnesium sulfate, concentrated with an evaporator in vacuo, and purified with silica gel column chromatography (ethyl acetate/hexane=8/2) to give compound (8a) in a 65% yield.
1H-NMR (300 MHz, DMSO-d6): δ 4.47 (dd, J=10.3 Hz, 8.61 Hz, 1H), 4.76 (s, 2H), 5.73 (s, 1H), 7.58 (t, J=4.29 Hz, 2H), 7.73 (t, J=4.39 Hz, 1H), 7.96 (d, J=4.56 Hz, 2H), 8.14 (s, 1H).

Example 7

Synthesis-1 of Compound (8b)

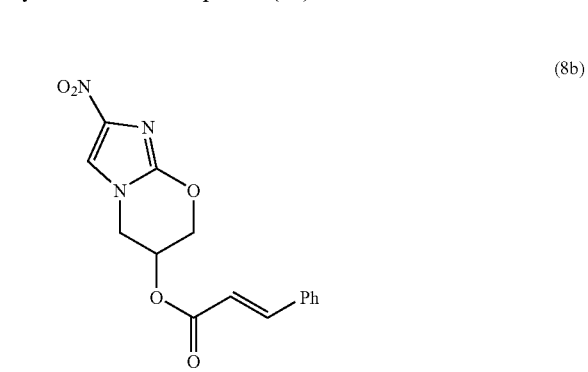

(8b)

Using compound (7b) as a starting material instead of compound (7a), the reaction was conducted in the same manner as in Example 6 to give compound (8b) in a 65% yield.
1H-NMR (300 MHz, DMSO-d6): δ 4.31 (d, J=13.9 Hz, 2H), 4.44 (d, J=5.74 Hz, 2H), 5.55 (s, 1H), 6.71 (d, J=15.9 Hz, 1H), 7.42 (t, J=2.48 Hz, 1H), 7.67–7.76 (m, 3H), 8.10 (s, 1H).

Example 8

Synthesis-2 of Compound (8b)

A reaction vessel was flame dried under an atmosphere of argon. Thereto were added compound (5a) (346 mg, 1 mmol), cinnamic acid (179 mg, 1.2 mmol) and DMAP (24.4 mg, 0.2 mmol), followed by addition of dichloromethane (5 ml) and the mixture was made completely homogenous. Thereto dicyclohexylcarbodiimide (DCC) (0.84 ml, 1 mmol) was dropped and the mixture was stirred for 20 hours at room temperature.

After confirming the completion of the reaction with TLC, TBAF in 1M tetrahydrofuran solution (1.5 ml, 1.5 mmol) was dropped thereto and the mixture was stirred for 3 hours.

After confirming the completion of the reaction with TLC, the reaction was quenched with an aqueous saturated sodium hydrogencarbonate solution (10 ml) and the reaction mixture was concentrated with an evaporator in vacuo, extracted with ethyl acetate (10 ml×3). The organic layer was washed with water (10 ml) and saturated brine (10 ml), successively, dried over anhydrous magnesium sulfate, concentrated with an evaporator in vacuo, and purified with silica gel column chromatography (ethyl acetate/hexane=8/2) to give compound (8b) in a 57% yield.

Example 9

Synthesis-3 of Compound (8b)

A reaction vessel was flame-dried under an atmosphere of argon. Thereto were added compound (5a) (346 mg, 1 mmol), cinnamic acid (179 mg, 1.2 mmol) and DMAP (24.4 mg, 0.2 mmol), followed by addition of tetrahydrofuran (2 ml) and the mixture was made completely homogenous. Thereto dicyclohexylcarbodiimide (DCC) (0.84 ml, 1 mmol) was dropped and the mixture was stirred for 5 hours at room temperature.

After confirming the completion of the reaction with TLC, TBAF in 1M tetrahydrofuran solution (1.5 ml, 1.5 mmol) was dropped thereto and the mixture was stirred for 13 hours.

After confirming the completion of the reaction with TLC, the reaction was quenched with an aqueous saturated sodium hydrogencarbonate solution (10 ml) and the reaction mixture was concentrated with an evaporator in vacuo, extracted with ethyl acetate (10 ml×3). The organic layer was washed with water (10 ml) and saturated brine (10 ml), successively, dried over anhydrous magnesium sulfate, concentrated with an evaporator in vacuo, and purified with silica gel column chromatography (ethyl acetate/hexane=8/2) to give compound (8b) in a 68% yield.

Example 10

Synthesis-1 of Compound (9a)

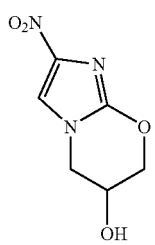

(9a)

A reaction vessel was flame dried under an atmosphere of argon. Thereto were added compound (8b) (315 mg, 1 mmol) and titanium tetraisopropoxide (27 mg, 0.1 mmol), followed by addition of methanol (40 ml), and the mixture was refluxed for 12 hours.

After confirming the completion of the reaction with TLC, in order to remove titanium tetraisopropoxide, the reaction mixture was filtered under suction with silica gel chromatography. The filtrate was concentrated with an evaporator in vacuo to give a solid mixture. Then suction filtration was carried out and the solid residue on a filter paper was washed with chloroform to give compound (9a) in a 93% yield.

1H-NMR (500 MHz, DMSO-d6): δ 3.97 (dt, J=13.1 Hz, 2.4 Hz, 1H), 4.20 (dd, J=13.1 Hz, 3.3 Hz, 1H), 4.28 (m, 1H), 4.32 (dt, J=11.6 Hz, 2.7 Hz, 1H), 4.42 (d, J=11.9 Hz, 1H), 5.67 (d, J=3.3 Hz, 1H), 8.01 (s, 1H)

Example 11

Synthesis-2 of Compound (9a)

Using bis(dibutylchlorotin)oxide (276 mg, 0.5 mmol) instead of titanium tetraisopropoxide, the reaction was conducted in the same manner as in Example 10 to give compound (9a) in a 77% yield.

Example 12

Synthesis-3 of Compound (9a)

A reaction vessel was flame-dried under an atmosphere of argon. Thereto were added compound (5a) (346 mg, 1 mmol), cinnamic acid (179 mg, 1.2 mmol) and DMAP (24.4 mg, 0.2 mmol), followed by addition of tetrahydrofuran (2 ml) and the mixture was made completely homogenous. Thereto DCC was dropped and the mixture was stirred for 5 hours at room temperature.

After confirming the completion of the reaction with TLC, thereto was added tetrahydrofuran (1.7 ml), and TBAF in 1M tetrahydrofuran solution (1.5 mmol) was dropped at 0° C. thereto and the mixture was stirred for 13 hours.

After confirming the completion of the reaction with TLC, titanium tetraisopropoxide (2.84 mg, 0.01 mmol) and methanol (7 ml) were added thereto and the mixture was refluxed for 16 hours.

After confirming the completion of the reaction with TLC, in order to remove titanium tetraisopropoxide, the reaction mixture was filtered under suction with silica gel chromatography, followed by concentration with an evaporator in vacuo. The reaction mixture was purified with silica gel column chromatography (ethyl acetate/hexane=9/1) and concentrated with an evaporator in vacuo to give a solid mixture. Then suction filtration was carried out and the solid residue on a filter paper was washed with chloroform to give compound (9a) in a 64% yield.

Example 13

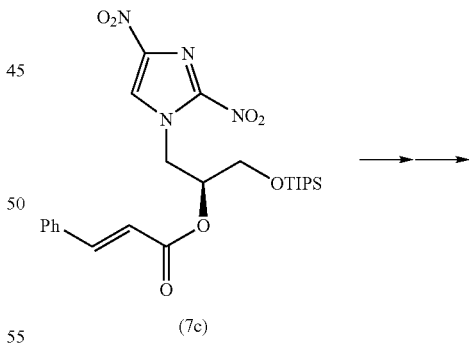

(7c)

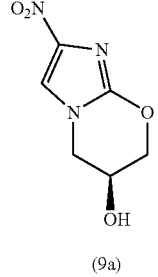

(9a)

Synthesis-4 of Compound (9a)

A reaction vessel was flame-dried under an atmosphere of argon. Thereto were added tetrahydrofuran (10 ml) and an optically active compound (7c) (1.037 g, 2 mmol, 98% ee), which was prepared in the same manner as Examples 1 and 2, by using triisopropylsilyl (TIPS) chloride instead of t-butyldimethylsilyl (TBS) chloride. To the mixture was dropped at 0° C. TBAF in 1M tetrahydrofuran (2.2 ml, 2.2 mmol), followed by stirring at room temperature for an hour.

After confirming the completion of the reaction with TLC, titanium tetraisopropoxide (5.7 mg, 0.02 mmol) and methanol (80 ml) were added thereto and the mixture was refluxed for 19 hours.

After confirming the completion of the reaction with TLC, the reaction mixture was concentrated with an evaporator in vacuo. The residue was purified with silica gel chromatography (ethyl acetate), concentrated with an evaporator in vacuo and crystallized from methanol to give compound (9a) in an 86% yield.

When compound (9a), which was acetylated was analyzed with HPLC (column: CHIRALCEL OD-H, eluent: isopropyl alcohol/hexane=⅜, flow rate: 0.5 ml/min), only peak of S isomer was observed at retention time 12.7 minutes (retention time of R isomer: 14.7 minutes).

INDUSTRIAL APLLICABILITY

The present invention is utilized in the field of the medicinal industry, for example, in a process for preparing a useful intermediate for PA-824 having antibacterial activity against Mycobacterium tuberculosis.

The invention being thus described, it will be obvious that the same may be varied in many ways. Such variations are not to be regarded as a departure from the scope of the invention, and all such modifications as would be obvious to one skilled in the art are intended to be included within the scope of the following claims.

What is claimed is:
1. A process for preparing an imidazopyran derivative of the following formula (9),

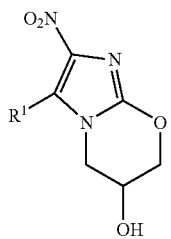

(9)

wherein $R^1$ is halogen atom, hydrogen atom, $C_1$–$C_3$ alkyl group, aryl group, or $C_1$–$C_3$ alkyl group substituted by aryl group,
which comprises reacting dinitroimidazole of the following formula (1),

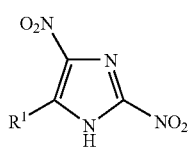

(1)

wherein $R^1$ is the same as defined above, with 2,3-epoxy-1-propanol of the following formula (2),

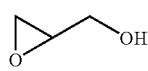

(2)

in the presence of a fluoride salt to prepare a diol compound of the following formula (3),

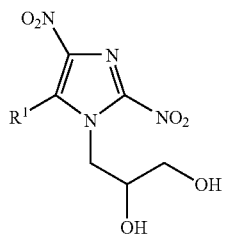

(3)

wherein $R^1$ is the same as defined above,
reacting this compound (3) with a silyl halide of the following formula (4), $$R^2R^3R^4SiX \qquad (4)$$

wherein $R^2$, $R^3$ and $R^4$ are independently $C_1$–$C_6$ alkyl group, aryl group or $C_1$–$C_3$ alkyl group substituted by aryl group, and X is halogen atom in the presence of a base to prepare a compound of the following formula (5),

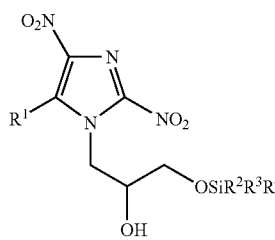

(5)

wherein $R^1$, $R^2$, $R^3$ and $R^4$ are the same as defined above, reacting this compound (5) with a compound of the following formula (6), $$R^5COY \qquad (6)$$

wherein $R^5$ is aryl group or $C_2$–$C_4$ alkenyl group substituted by aryl group, and Y is hydroxy group, halogen atom or alkoxy group,
to prepare a compound of the following formula (7),

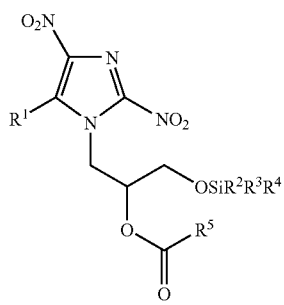

(7)

wherein $R^1$, $R^2$, $R^3$, $R^4$ and $R^5$ are defined above, desilylating and cyclizing this compound (7) to prepare a compound of the following formula (8),

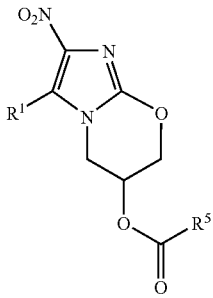

(8)

wherein R¹ and R⁵ are the same as defined above,
and then deprotecting this compound (8) in the presence of metallic catalyst to prepare above imidazopyran derivative (9).

2. The process for preparing a compound according to claim 1 wherein dinitroimidazole (1) and 2,3-epoxy-1-propanol (2) are reacted in the presence of a fluoride salt in the absence of a solvent.

3. A process for preparing an imidazopyran ester derivative of the formula (8),

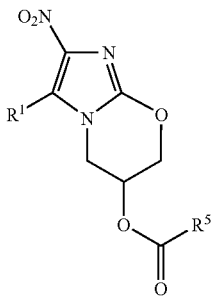

(8)

wherein R¹ and R⁵ are the same as defined in claim 1, which comprises reacting a compound of the formula (5),

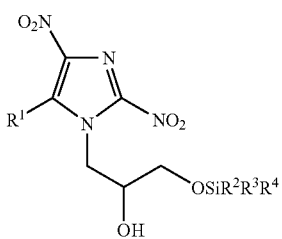

(5)

wherein R¹, R², R³ and R⁴ are the same as defined in claim 1,
with a compound of the formula (6),

R⁵COY   (6)

wherein R⁵ and Y are the same as defined in claim 1, to prepare a compound of the following formula (7),

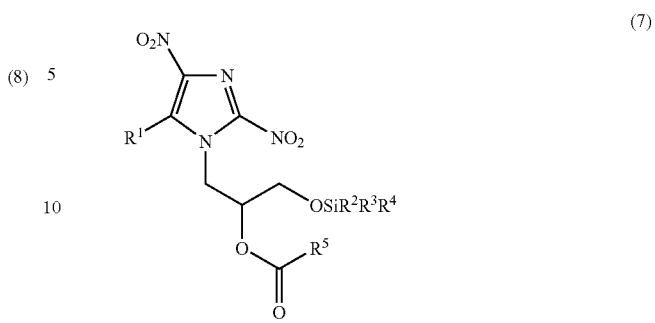

(7)

wherein R¹, R², R³, R⁴ and R⁵ are the same as defined in claim 1,
and then desilylating and cyclizing this compound (7) to prepare above compound (8).

4. A process for preparing an imidazopyran derivative of the formula (9),

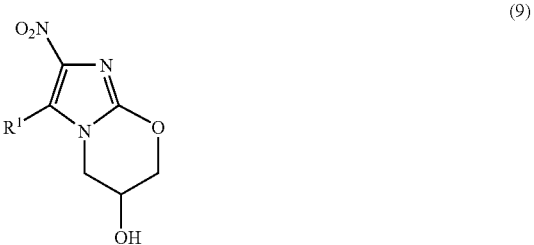

(9)

wherein R¹ is the same as defined in claim 1,
which comprises reacting a compound of the following formula (5),

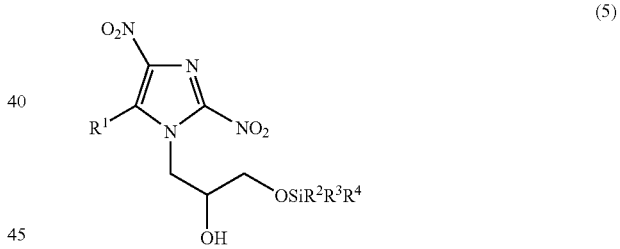

(5)

wherein R¹, R², R³ and R⁴ are the same as defined in claim 1,
with a compound of the following formula (6),

R⁵COY   (6)

wherein R⁵ and Y are the same as defined in claim 1,
to prepare a compound of the following compound (7),

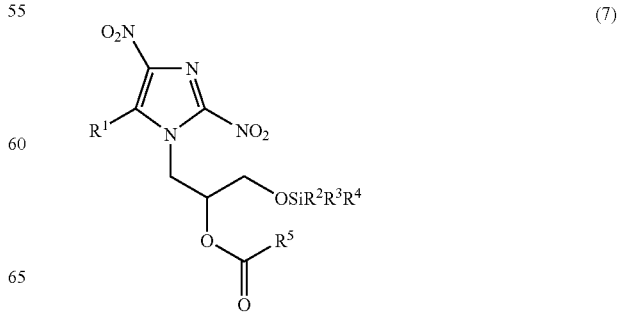

(7)

wherein $R^1$, $R^2$, $R^3$, $R^4$ and $R^5$ are the same as defined in claim 1, desilylation and cyclization this compound (7) to prepare a compound of the following formula (8),

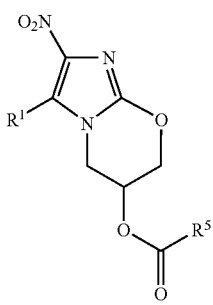

(8)

wherein $R^1$ and $R^5$ the same as defined in claim 1, and then deprotecting this compound (8) in the presence of metallic catalyst to prepare above compound (9).

5. A process for preparing an imidazopyran ester derivative of the following formula (8),

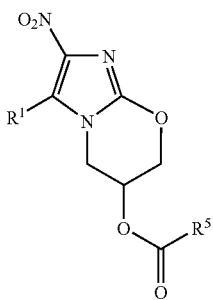

(8)

wherein $R^1$ and $R^5$ are the same as defined in claim 1, which comprises desilylating and cyclizing a compound of the following formula (7),

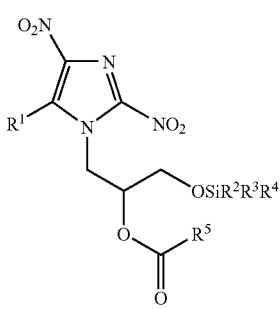

(7)

wherein $R^1$, $R^2$, $R^3$, $R^4$ and $R^5$ are the same as defined in claim 1, to prepare above compound (8).

6. The process for preparing a compound according to claim 1 wherein the desilylation and cyclization is conducted in the presence of a fluoride salt.

7. A process for preparing an imidazopyran derivative of the following formula (9),

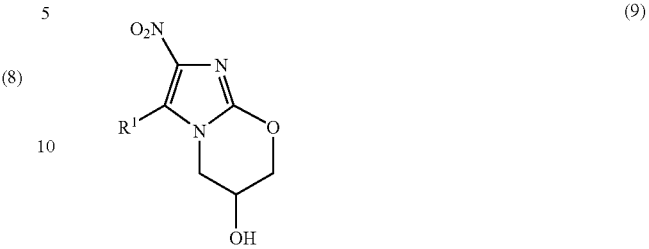

(9)

wherein $R^1$ is the same as defined in claim 1, which comprises deprotecting a compound of the following formula (8),

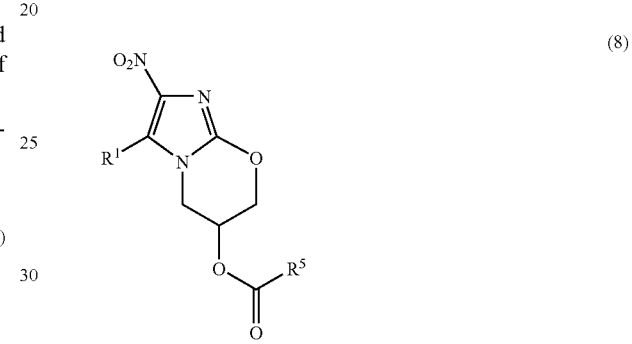

(8)

wherein $R^1$ and $R^5$ are the same as defined in claim 1, in the presence of metallic catalyst to prepare above compound (9).

8. The process for preparing a compound according to claim 1 wherein the metallic catalyst is organic metallic catalyst having Lewis acidity.

9. The process for preparing a compound according to claim 1 wherein the final product is prepared in an optically active isomer starting from an optically active isomer as a starting material.

10. An imidazopyran ester derivative of the formula (8),

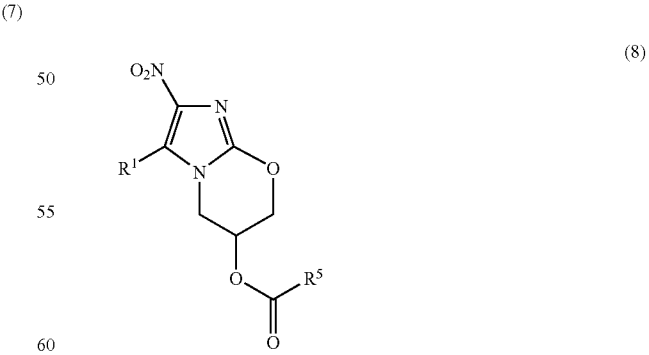

(8)

wherein $R^1$ and $R^5$ are the same as defined in claim 1, or its optically active isomer.

11. The process for preparing a compound according to claim 3 wherein the desilylation and cyclization is conducted in the presence of a fluoride salt.

12. The process for preparing a compound according to claim 4 wherein the desilylation and cyclization is conducted in the presence of a fluoride salt.

13. The process for preparing a compound according to claim 5 wherein the desilylation and cyclization is conducted in the presence of a fluoride salt.

14. The process for preparing a compound according to claim 4 wherein the metallic catalyst is organic metallic catalyst having Lewis acidity.

15. The process for preparing a compound according to claim 7 wherein the metallic catalyst is organic metallic catalyst having Lewis acidity.

16. The process for preparing a compound according to claim 3 wherein the reaction is carried out in one pot without isolating and purifying the products in each step.

17. The process for preparing a compound according to claim 4 wherein the reaction is carried out in one pot without isolating and purifying the products in each step.

18. The process for preparing a compound according to claim 4 wherein the final product is prepared in an optically active isomer starting from an optically active isomer as a starting material.

* * * * *